United States Patent [19]

Lerch et al.

[11] Patent Number: 4,882,329

[45] Date of Patent: Nov. 21, 1989

[54] ALKOXYPHENYLINDOLINONE DERIVATIVES, MEDICAMENTS CONTAINING THEM AND THEIR USE

[75] Inventors: Ulrich Lerch, Hofheim am Taunus; Rainer Henning, Hattersheim am Main; Joachim Kaiser, Frankfurt am Main, all of Fed. Rep. of Germany

[73] Assignee: Hoechst Aktiengesellschaft, Frankfurt am Main, Fed. Rep. of Germany

[21] Appl. No.: 303,996

[22] Filed: Jan. 30, 1989

Related U.S. Application Data

[63] Continuation of Ser. No. 898,117, Aug. 20, 1986, abandoned.

[30] Foreign Application Priority Data

Aug. 22, 1985 [DE] Fed. Rep. of Germany ....... 3529994

[51] Int. Cl.[4] ................. A61K 31/495; C07D 403/12; C07D 401/14
[52] U.S. Cl. .................................... 514/253; 544/360; 544/373; 544/295; 548/486; 546/201; 546/256; 546/273; 514/333; 514/339; 514/418; 560/250; 564/170
[58] Field of Search ................. 544/373, 360; 514/253

[56] References Cited

U.S. PATENT DOCUMENTS

| | | | |
|---|---|---|---|
| 2,759,935 | 8/1956 | Speeter | 544/373 |
| 3,865,828 | 2/1975 | Korosi et al. | 544/360 |
| 4,015,002 | 3/1977 | Pesson et al. | 260/325 |
| 4,053,483 | 10/1977 | Hosta Pujol et al. | 260/325 R |
| 4,110,465 | 8/1978 | Holmes | 548/486 |
| 4,234,584 | 11/1980 | Lattrell et al. | 544/373 |
| 4,374,990 | 2/1983 | Weber et al. | 544/372 |
| 4,542,148 | 9/1985 | Kuch et al. | 514/418 |
| 4,595,685 | 6/1986 | Henning et al. | 544/51 |
| 4,624,963 | 11/1986 | Kruse et al. | 514/255 |
| 4,650,811 | 3/1987 | Guillaume et al. | 544/373 |

FOREIGN PATENT DOCUMENTS

| | | | |
|---|---|---|---|
| 2451592 | 6/1975 | Fed. Rep. of Germany . | |
| 2507604 | 12/1982 | France | 514/255 |
| 1361863 | 7/1974 | United Kingdom | 514/255 |

*Primary Examiner*—Mukund J. Shah
*Assistant Examiner*—Emily Bernhardt
*Attorney, Agent, or Firm*—Finnegan, Henderson, Farabow, Garrett, & Dunner

[57] ABSTRACT

Calcium antagonists of the formula

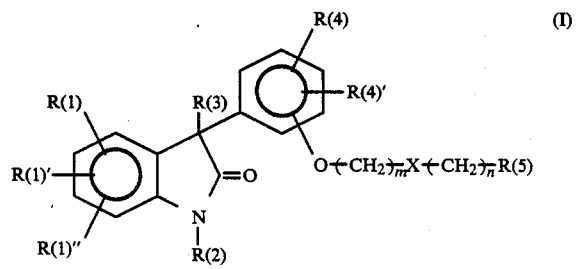

with R(1), R(2), R(3) and R(4) being, inter alia, H, alkyl, alkoxy, halogen, in some cases phenyl; m being 1–4; n being 0–3; X being $CH_2$, O, S, CO, CHOH or $CR_2$, and R(5) being various groups containing nitrogen atoms, are described.

They are obtained by reaction of compounds II which are likewise new and which contain in place of R(5) a leaving group Y (Cl, Br, I) with the appropriate (cyclic) amino compound.

Another synthesis comprises reaction of the appropriate indolinone derivative IV which has a non-etherified hydroxyl group with a side chain which contains a terminal leaving group Z (Cl, Br, I) in the presence of a base.

Furthermore, indolinone derivatives VI with an ether side chain with a terminal epoxide group can be reacted with (cyclic) amines to give compounds I.

5 Claims, No Drawings

ALKOXYPHENYLINDOLINONE DERIVATIVES, MEDICAMENTS CONTAINING THEM AND THEIR USE

This application is a continuation of application Ser. No. 898,117 filed Aug. 20, 1986, now abandoned.

It is known that compounds which impede the influx of calcium ions into cells can be used as therapeutic agents for the treatment of various diseases, in particular of the cardiovascular system of humans and other warm-blooded species.

The synthesis of 3-arylindolin-2-ones is known; however, 3-arylindolin-2-ones substituted by a basic ether group on the 3-phenyl radical are not known; furthermore, such indolinone compounds having a calcium-antagonistic action are not known.

The invention relates to indolinone derivatives of the formula I, which have such an action

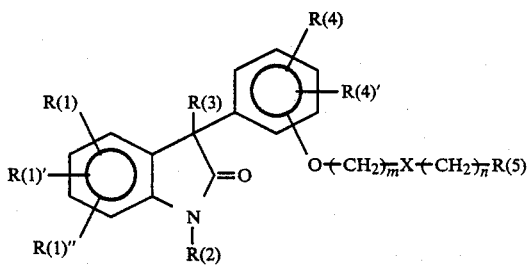

and in which

R(1), R(1)' and R(1)" are identical or different and are independent of one another and denote hydrogen, $(C_1-C_4)$-alkyl, $(C_1-C_3)$-alkoxy, F, Cl, Br, $CF_3$, nitro, hydroxyl, acetamido or amino, R(2) denotes hydrogen, $(C_1-C_{10})$-alkyl, straight-chain or branched, $(C_3-C_{10})$-alkenyl, straight-chain or branched, phenyl-$(C_1-C_4)$-alkyl, the phenyl ring being unsubstituted or substituted by one, two or three substituents from the group comprising $(C_1-C_4)$-alkyl, $(C_1-C_3)$-alkoxy, F, Cl, $CF_3$, $(C_1-C_2)$ alkylenedioxy or nitro, R(3) denotes hydrogen, $(C_1-C_{15})$-alkyl, straight-chain or branched, $(C_3-C_{15})$-alkenyl, straight-chain or branched, $(C_4-C_8)$-cycloalkyl, $(C_4-C_8)$-cycloalkyl-$(C_1-C_4)$-alkyl, phenyl or phenyl-$(C_1-C_4)$-alkyl, the phenyl radical being unsubstituted or substituted by one, two or three substituents from the group comprising $(C_1-C_4)$-alkyl, $(C_1-C_3)$-alkoxy, F, Cl, $CF_3$, $(C_1-C_2)$-alkylenedioxy and nitro, R(4) and R(4)' denote, independently of one another, identical or different hydrogen $(C_1-C_4)$-alkyl, $(C_1-C_3)$-alkoxy, F, Cl, $CF_3$, nitro, hydroxyl, acetamido or amino, m denotes 1, 2, 3 or 4, n denotes 0, 1, 2 or 3 but where X is a heteroatom only 2 or 3

X is a $CH_2$ group, oxygen, sulfur, a carbonyl group, a CH(OH) group or a group

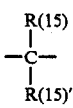

in which

R(15) and R(15)' are identical or different and denote hydrogen or $(C_1-C_4)$-alkyl, R(5) denotes one of the following groups

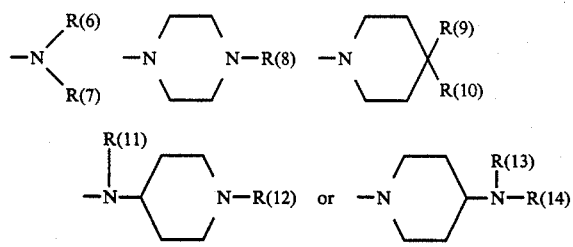

in which

R(6) and R(7), independently of one another, denote identical or different hydrogen, $(C_1-C_{10})$-alkyl, $(C_4-C_8)$-cycloalkyl, $(C_4-C_8)$-cycloalkyl-$(C_1-C_4)$-alkyl, pyridyl-$(C_1-C_4)$-alkyl, phenyl-$(C_1-C_6)$-alkyl, benzhydryl or benzhydryl-$(C_1-C_4)$-alkyl, the phenyl radicals each being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, R(8) denotes hydrogen, $(C_1-C_{10})$-alkyl, straight-chain or branched, $(C_1-C_8)$-alkanoyl, pyridyl, pyrimidinyl, phenyl, phenyl-$(C_1-C_4)$-alkyl, phenyl-$(C_3-C_5)$-alkenyl, benzhydryl or benzhydryl-$(C_1-C_4)$-alkyl, phenyl-$(C_1-C_4)$-alkanoyl or benzoyl, the phenyl radicals each being unsubstituted or substituted by one, two or three radicals from the group comprising $(C_1-C_4)$alkyl, $(C_1-C_4)$-alkoxy, $(C_1-C_2)$-alkylenedioxy, F, Cl, Br, $CF_3$ or hydroxyl, R(9) denotes hydrogen, $(C_1-C_{10})$-alkyl, phenyl, phenyl-$(C_1-C_4)$-alkyl, the phenyl radical in each case being unsubstituted or substituted by one, two or three radicals from the group comprising $(C_1-C_4)$L alkyl, $(C_1-C_4)$-alkoxy, $(C_1-C_2)$-alkylenedioxy, F, Cl, Br, $CF_3$ or hydroxyl, R(10) denotes hydrogen, hydroxyl or $(C_1-C_4)$-alkoxy, and R(11) and R(12) or R(13) and R(14), independently of one another, denote identical or different hydrogen, $(C_1-C_{10})$-alkyl, straight-chain or branched, $(C_1-C_6)'$ alkanoyl, phenyl-$(C_1-C_4)$-alkyl, benzhydryl or benzhydryl-$(C_1-C_4)$-alkyl, phenyl-$(C_1-C_4)$-alkanoyl or benzoyl, the phenyl radicals each being unsubstituted or substituted by one, two or three radicals from the group comprising $(C_1-C_4)$-alkyl, $(C_1-C_4)$-alkoxy, $(C_1-C_2)$-alkylenedioxy, F, Cl, Br, $CF_3$ or hydroxyl, and to the salts of the compounds of the formula I with pharmaceutically acceptable acids.

Preferred compounds of the formula I are those in which

R(1) and R(1)' are identical or different and, independently of one another, denote hydrogen, methyl, ethyl, methoxy, ethoxy, fluorine, chlorine, $CF_3$, nitro or acetamido, R(1)" denotes hydrogen, R(2) denotes hydrogen, $(C_1-C_6)$-alkyl, straight-chain or branched, allyl, methallyl, benzyl, phenethyl, 4-methoxybenzyl, 3,4-dimethoxybenzyl, 3,4,5-trimethoxybenzyl, 3,4-methylenedioxybenzyl, R(3) denotes hydrogen, $(C_1-C_{12})$-alkyl, straight-chain or branched, allyl, methallyl, $(C_5-C_7)$-cycloalkyl, $(C_5-C_7)$-cycloalkyl-$(C_1-C_4)$-alkyl, benzyl, methylbenzyl, fluorobenzyl, methoxybenzyl, dimethoxybenzyl, phenylethyl, R(4) denotes hydrogen, methyl, methoxy, ethoxy, chlorine, nitro, hydroxyl, acetamido or amino, R(4)' denotes hydrogen, m denotes 1, 2, 3 or 4, n denotes 0, 1, 2 or 3, but where X denotes a heteroatom only 2 or 3

X denotes a CH$_2$ group, oxygen, sulfur, a carbonyl group, a CH(OH) group or a group

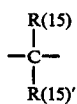

in which

R(15) and R(15)' are identical or different and denote hydrogen, methyl or ethyl, R(5) denotes one of the group

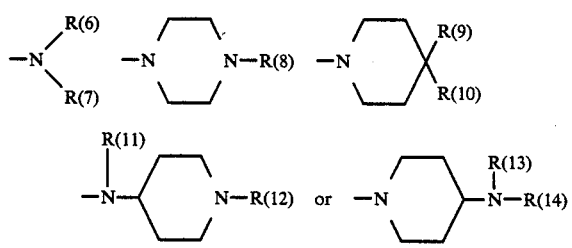

in which

R(6) denotes hydrogen, methyl, ethyl, propyl, isopropyl,

R(7) denotes hydrogen, methyl, ethyl, propyl, isopropyl, cyclopentylethyl, cyclohexylethyl, phenyl-(C$_1$-C$_4$)-alkyl, benzhydryl or benzhydryl-(C$_1$-C$_4$)-alkyl, the phenyl radicals each being unsubstituted or substituted by one, two or three radicals from the group comprising (C$_1$-C$_4$)-alkyl, (C$_1$-C$_4$)-alkoxy, (C$_1$-C$_2$)-alkylenedioxy, F, Cl, CF$_3$ or hydroxyl, or pyridyl-(C$_1$-C$_4$)-alkyl, R(8) denotes hydrogen, (C$_1$-C$_6$)-alkyl, straight-chain or (C$_1$-C$_6$)-alkanoyl, phenyl, it being possible for the phenyl radical to be substituted by or two radicals from the group comprising (C$_1$-C$_4$)-alkyl, (C$_1$-C$_4$)-alkoxy, (C$_1$-C$_2$)-alkylenedioxy, F, Cl, CF$_3$ or hydroxyl, or denotes phenyl-(C$_1$-C$_4$)alkyl, phenyl-(C$_3$-C$_5$)-alkenyl, benzhydryl or benzhydryl-(C$_1$-C$_4$)-alkyl, phenyl-(C$_1$-C$_4$)-alkanoyl or benzoyl, the phenyl radicals each being unsubstituted or substituted by one, two or three radicals from the group comprising methyl, ethyl, methoxy, ethoxy, (C$_1$-C$_2$)-alkylenedioxy, F, Cl, CF$_3$ or hydroxyl, R(9) denotes phenyl, phenyl-(C$_1$-C$_4$)-alkyl, the phenyl radical in each case being unsubstituted or substituted by one, two or three radicals from the group comprising (C$_1$-C$_4$)-alkyl, (C$_1$-C$_4$)-alkoxy, (C$_1$-C$_2$)-alkylenedioxy, F, Cl, CF$_3$ or hydroxyl, R(10) denotes hydrogen, hydroxyl or methoxy, R(11), R(12), R(13) and R(14) denote identical or different hydrogen, (C$_1$-C$_8$)-alkyl, (C$_1$-C$_6$)-alkanoyl, phenyl-(C$_1$-C$_4$)-alkyl, benzhydryl or benzhydryl-(C$_1$-C$_4$)-alkyl, it being possible for the phenyl radicals each to be unsubstituted or substituted by one, two or three radicals from the group comprising methyl, ethyl, methoxy, ethoxy, (C$_1$-C$_2$)-alkylenedioxy, F, Cl, CF$_3$ or hydroxyl or denotes phenyl-(C$_1$-C$_4$)-alkanoyl or benzoyl, the phenyl radicals each being unsubstituted or substituted by one, two or three radicals from the group comprising methyl, ethyl, methoxy, ethoxy, (C$_1$-C$_2$)-alkylenedioxy, F, Cl, CF$_3$ or hydroxyl, and the salts of these compounds of the formula I with pharmaceutically acceptable acids.

Particularly preferred compounds of the formula I are those in which

R(1) denotes hydrogen, methyl, methoxy, fluorine or chlorine,

R(1)' denotes hydrogen methoxy,

R(1)" denotes hydrogen,

R(2) denotes hydrogen, methyl, ethyl, propyl, isopropyl, butyl, sec. butyl, isobutyl, benzyl, phenethyl, R(3) denotes hydrogen, (C$_1$-C$_{12}$)-alkyl, straight-chain or branched, cyclopentyl, cyclohexyl, cyclopentylmethyl, cyclohexylmethyl, allyl, methallyl, benzyl, methylbenzyl, fluorobenzyl, methoxybenzyl, dimethosxybenzyl, phenylethyl, R(4) denotes hydrogen, methoxy, methyl, chlorine, nitro or hydroxyl, R(4)' denotes hydrogen, m denotes 1, 2 or 3, n denotes 0, 1 or 2, but where X denotes a heteroatom only 2

X denotes a CH$_2$ group, oxygen, a carbonyl group, a CH(OH) group or a group

in which

R(15) and R(15)' are identical or different and denote hydrogen or methyl,

R(5) denotes one of the following groups

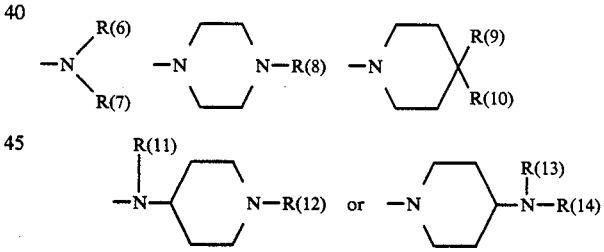

in which

R(6) denotes hydrogen or methyl,

R(7) denotes phenyl-(C$_1$-C$_4$)-alkyl, benzhydryl or benzhydryl-(C$_1$-C$_4$)-alkyl, the phenyl radical in each case being unsubstituted or substituted by one, two or three radicals from the group comprising methyl, methoxy, fluorine, chlorine, methylenedioxy or hydroxyl, R(8) denotes (C$_1$-C$_6$)-alkyl, straight-chain or branched, (C$_1$-C$_6$)-alkanoyl, phenyl, phenyl-(C$_1$-C$_4$)-alkyl, benzhydryl or benzhydryl-(C$_1$-C$_4$)-alkyl, phenyl-(C$_1$-C$_4$) alkanoyl or benzoyl, the phenyl radicals each being unsubstituted or substituted by one, two or three radicals from the group comprising methyl, methoxy, ethoxy, methylenedioxy, fluorine, chlorine or hydroxyl, R(9) denotes phenyl, the phenyl radical being unsubstituted or substituted by one, two or three radicals from the group comprising methyl, methoxy, fluorine, chlorine, methylenedioxy or hydroxyl.

R(10) denotes hydrogen, hydroxyl or methoxy,

R(11), R(12), R(13) and R(14) are identical or different and denote hydrogen, (C₁-C₆)-alkyl, (C₁-C₆)-alkanoyl, phenyl-(C₁-C₄)-alkyl, benzhydryl or benzhydryl-(C₁-C₄)-alkyl, phenyl-(C₁-C₄)-alkanoyl or benzoyl, the phenyl radicals each being unsubstituted or substituted by one, two or three radicals from the group comprising methyl, methoxy, methylenedioxy, fluorine, chlorine or hydroxyl, and the salts of these compounds of the formula I with pharmaceutically acceptable acids.

Those pharmaceutically acceptable acids which are suitable are inorganic acids such as hydrochloric acid, hydrobromic acid, hydroiodic acid, sulfuric acid, phosphoric acid or nitric acid, or organic acids such as tartaric acid, malic acid, lactic acid, maleic acid, fumaric acid, malonic acid, oxalic acid, gluconic acid, camphorsulfonic acid, benzenesulfonic acid, acetic acid, propionic acid or p-toluenesulfonic acid.

The compounds of the formula I have asymmetric carbon atoms and can thus occur as enantiomers or diastereomers. The invention embraces both the pure isomers and mixtures thereof. These mixtures of diastereomers can be separated into the components by conventional methods, for example selective crystallization from suitable solvents, or chromatography on silica gel or alumina. Racemates can be resolved into the individual enantiomers by customary methods, for example by salt formation with optically active acids such as camphorsulfonic acid or dibenzoyltartaric acid and selective crystallization, or by derivatization with suitable optically active reagents, separation of the diastereomeric derivatives and cleavage again.

The invention also relates to processes for the preparation of compounds of the formula I, which comprise (a) reaction of a compound of the formula II

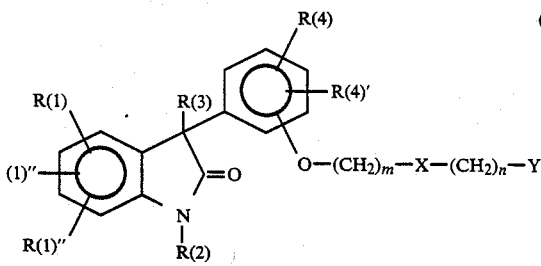

in which R(1), R(1)', R(1)'', R(2), R(3), R(4), R(4)', X, m and n have the same meaning as in formula I, and in which Y denotes a leaving group which can undergo nucleophilic displacement, in particular a chlorine, bromine or iodine atom, a sulfonyl radical, preferably a methanesulfonyl radical, a benzenesulfonyl radical, a toluenesulfonyl radical or a trifluoromethanesulfonyl radical, with one of the compounds of the formulae IIIa, IIIb, IIIc, IIId or IIIe

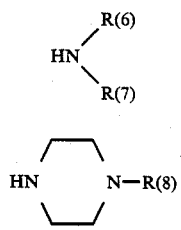

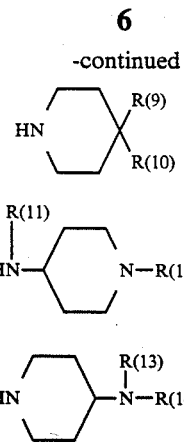

in which R(6), R(7), R(8), R(9), R(10), R(11), R(12), R(13) and R(14) have the same meaning as in formula I, under the conditions of a nucleophilic substitution, preferably in a polar organic solvent such as an alcohol, preferably methanol, ethanol, propanol or isopropanol, or a lower ketone, preferably acetone or methyl ethyl ketone, or dimethylformamide, dimethyl sulfoxide or sulfolane, or a hydrocarbon, preferably toluene, with or without the presence of an auxiliary base to capture the acid which is being formed, preferably in the presence of potassium carbonate, sodium carbonate, triethylamine, N-ethylmorpholine or pyridine, at a temperature between 0° and 160° C., preferably between 20° and 120° C., or (b) reaction of a compound of the formula IV

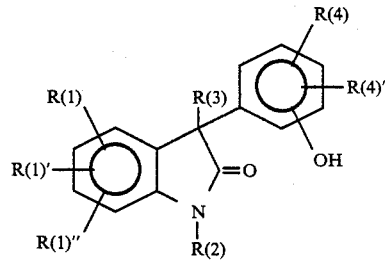

in which R(1), R(1)', R(1)'', R(2), R(3), R(4) and R(4)' have the same meaning as in formula I, with a compound of the formula V $$Z-(CH_2)_m-X-(CH_2)_n-R(5) \quad V$$

in which Z has the same definition as Y in formula II, and in which R(5), X, m and n have the same meaning as in formula I, either in a polar aprotic solvent such as dimethylformamide, dimethyl sulfoxide, tetrahydrofuran, sulfolane or N-methylpyrrolidone, in the presence of a strong base such as sodium hydride, potassium hydride, sodamide, lithium diisopropylamide, butyllithium or lithium hexamethyldisilazide, at a temperature between −40° and +60° C., preferably between −10° and −30° C., or in a protic or aprotic polar organic solvent such as a lower alcohol, for example methanol, ethanol, isopropanol, or a lower ketone, preferably acetone or methyl ethyl ketone, or in dimethylformamide, in the presence of a weak to moderately strong base such as an alkali metal or alkaline earth metal hydroxide or carbonate, or an amine such as, for example, triethylamine, N-ethylmorpholine, N-methyldiisopropylamine or pyridine, at a temperature between 0 and 160° C., preferably between 20° and 120° C., or (c) reaction of a compound of the formula VI

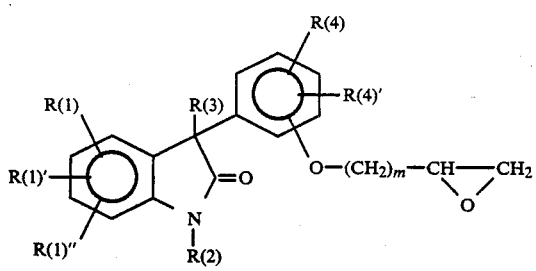

in which R(1), R(1)', R(1)", R(2), R(3), R(4), R(4)' and m have the same meaning as in formula I, with amines of the formula IIIa–IIIe without a solvent or in the presence of a, preferably polar, solvent such as methanol, isopropanol, acetone, THF or dimethylformamide, resulting in compounds of the formula I in which x=CHOH and n=1, or (d) reaction of a compound of the formula VII

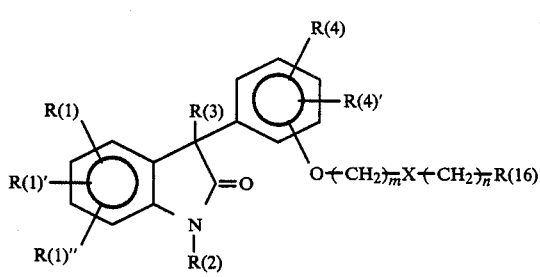

in which R(1), R(1)', R(1)", R(2), R(3), R(4), R(4)', X, m and n have the same meaning as in formula I, and in which R(16) denotes one of the following groups

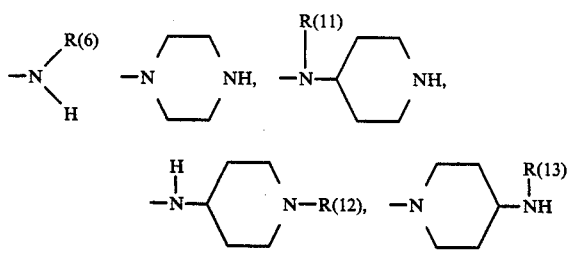

in which R(6), R(11), R(12) and R(13) have the same meaning as in formula I, with alkylating or acylating agents by methods known from the literature, resulting in compounds of the formula I.

Compounds of the formula II, which are likewise new and to which the invention relates, are obtained from substituted anilines of the formula VIII

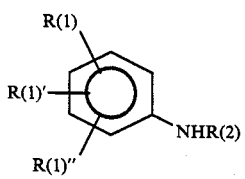

in which R(1), R(1)', R(1)" and R(2) have the same meaning as in formula I, in which formula VIII at least one position ortho to the amino group must be free, by reaction with a compound of the formula IX

in which R(3), R(4), R(4)' have the same meaning as in formula I, R(17) represents a protective group which can be eliminated under mild conditions such as, for example, a methyl, benzyl or acetyl group, V denotes OH, Cl or O-($C_1$-$C_4$)-alkyl and W denotes OH, OAc, chlorine or bromine, by the generally known methods for the synthesis of amides from amines and carboxylic acid derivatives, there being formation of compounds of the formula X

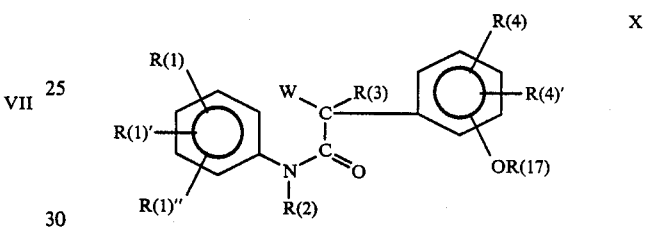

in which R(1), R(1)', R(1)", R(2), R(3), R(4) and R(4)' have the same meaning as in formula I, and R(17) and W have the same meaning as in formula IX. Where W in formula X denotes a O-acetyl group it is expedient, before the subsequent cyclization reaction, to convert this into a free hydroxyl group. This can be carried out in a known manner by alkaline hydrolysis, for example with bases such as ammonia, potassium hydroxide or sodium carbonate in a solvent such as, for example, methanol, THF or water.

Subsequent reaction of the compounds of the formula X with dehydrating agents such as, for example, polyphosphoric acid or concentrated sulfuric acid, or with Lewis acid catalysts, such aluminum chloride, titanium tetrachloride, tin tetrachloride, or $BF_3$-etherate results in compounds of the formula XI

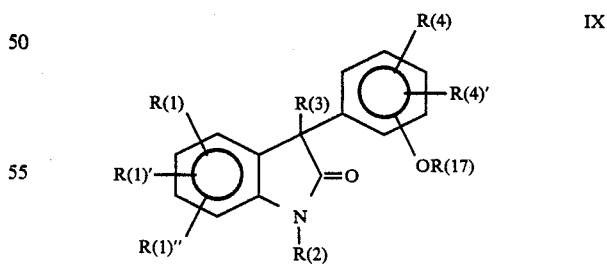

in which R(1), R(1)', R(1)", R(2), R(3), R(4) and R(4)' have the same meaning as in formula I and R(17) has the same meaning as in formula IX.

Where R(3) in formula XI denotes hydrogen, it is expedient to introduce the radicals R(3), which do not equal H, by alkylation with a compound of the formula XII

R(3)—Y           XII in which R(3) has the same meaning as in formula I (but R(3) does not equal H), and Y is defined in formula II, expediently in the presence of a base such as, for example, sodium hydride, sodium ethylate or a lithium amide, there being formation of compounds of the formula XI with R(3) not equal to H.

It is likewise possible to introduce radicals R(2) which do not denote hydrogen into compounds of the formula XI in which R(2) denotes hydrogen by alkylation, for example using a R(2) halide or R(2) sulfonate in the presence of a base, such as, for example, sodium hydride or potassium carbonate, with a phase-transfer catalyst, halide denoting chloride, bromide or iodide.

The compounds of the formula IV are obtained from compounds of the formula XI by elimination of the protective group R(17) under suitable conditions, for example by catalytic hydrogenation for the benzyl group, or reaction with boron tribromide, trimethyliodosilane or pyridine hydrochloride for the methyl group, or potassium carbonate in alcoholic solution for the acetyl group.

Compounds of the formula II can be prepared from compounds of the formula IV by reaction with compounds of the formula XIII

$$Q-(CH_2)_m-X-(CH_2)_n-Y \qquad XIII$$

in which X, and n have the same meaning as in formula I, Y has the same meaning as in formula II, and Q has the same definition as Y in formula II, in the presence of bases such as, for example, sodium hydroxide, potassium carbonate, sodium methylate or potassium tertiary-butylate, in a solvent such as, for example, tetrahydrofuran, methanol, dimethoxyethane, acetone, methyl ethyl ketone, dimethylformamide or dimethyl sulfoxide.

Compounds of the formula VI are obtained from compounds of the formula IV with, for example, epichlorohydrin and base (for m=1) by known methods, or by alkylation of compounds of the formula IV with compounds of the formula XIV

$$Y-(CH_2)_m-CH=CH_2 \qquad XIV$$

in which m has the same meaning as in formula I and Y has the same definition as formula II, there being formation of compounds of the formula XV

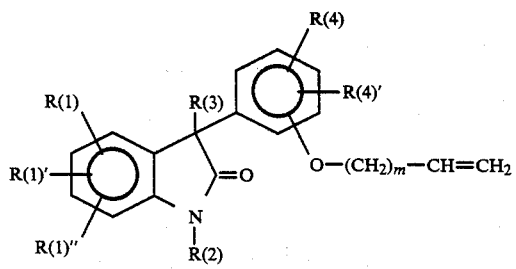

in which R(1), R(1)', R(1)'', R(2), R(3), R(4), R(4)' and m have the same meaning as in formula I. Subsequent epoxidation of the compounds XV by known methods, for example with m-chloroperbenzoic acid in methylene chloride, provides compounds of the formula VI.

The compounds of the formula I, according to the invention, have blood-pressure lowering, in particular calciumantagonistic actions, and can thus be used for the treatment of all disease states deriving from a disturbance in the calcium balance in a warm-blooded animal.

Their calcium-antagonistic activity can be shown in the biochemical test model of displacement of tritium-labeled nitrendipine.

This entails membrane preparations which contain isolated calcium channels being loaded with labeled substance.

After incubation with the test substance, the radioactivity which has been released into the supernatant solution is determined. In this model, the compounds of the formula I, according to the invention, exhibit $IC_{50}$ values of $10^{-6}$ molar to $10^{-9}$ molar. The compounds of the formula I are likewise very active in other test models with which a calcium-antagonistic action can be detected, for example the coronary blood flow in the isolated guinea-pig heart, or the action potential of the isolated guinea-pig papillary muscle.

The compounds of the formula I, according to the invention, and their pharmacologically tolerated salts diminish the influx of calcium ions into cells and are thus suitable for the treatment of the cardiovascular system with appropriate disorders, for example with various forms of angina pectoris, tachycardia, cardiac arrhythmias and high blood pressure. They are active within a wide dose range. The level of the dose administered depends on the type of desired treatment, on the mode of administration, on the condition, on the type and on the size of the mammal which is treated. On oral administration, satisfactory results are achieved with doses of 0.01 mg and, preferably, of 0.1 mg and above and up to 100 mg, preferably up to 20 mg, of a compound of the formula I per kg of body weight. In humans, the daily dose varies between 10 and 800 mg, preferably 20 to 500 mg, it being possible to administer individual doses of 5 to 200 mg, preferably once to three times a day.

The dose for intravenous and intramuscular administration is 1 to 300 mg, preferably 5 to 150 mg, a day.

The pharmacologically utilizable compounds of the present invention and their salts can be used for the preparation of pharmaceutical products which contain an active amount of the active substance together with vehicles, and which are suitable for enteral and parenteral administration. Use is preferably made of tablets or gelatin capsules which contain the active compound together with diluents, for example lactose, dextrose, sucrose, mannitol, sorbitol, cellulose and/or glycine, and lubricants such as silica, talc, stearic acid or its salts, such as magnesium or calcium stearate and/or polyethylene glycol. Tablets likewise contain binders such as magnesium aluminum silicate, starch, gelatin, tragacanth, methylcellulose, sodium carboxymethylcellulose and/or polyvinylpyrrolidone and, if necessary, colorants, flavorings and sweeteners. Injectable solutions are preferably isotonic aqueous solutions or suspensions which can be sterilized and may contain auxiliaries such as preservatives, stabilizers, wetting and/or emulsifying agents, solubilizers, salts for regulation of the osmotic pressure and/or buffer substances. The pharmaceutical products according to the invention, which, if desired, can contain other pharmacologically valuable substances, are prepared by, for example, conventional mixing, granulating and coating processes, and contain 0.1% to about 75%, preferably about 1% to about 50%, of the active compound.

The examples which follow are intended to illustrate the invention but without limiting it to these examples.

EXAMPLE 1

3-Benzyl-3-[2-(4-(N-(2-(3,4-dimethoxyphenyl)ethyl)-N-methylamino)butoxy)phenyl]-1-methylindolin-2-one hydrochloride (a)

N-Methyl-N-phenyl-2-methoxy-O-acetylmandelamide 22.4 g (0.1 mol) of 2-methoxy-O-acetylmandelic acid were heated under reflux with 100 ml of toluene and 28.8 ml (0.4 mol) of thionyl chloride in the presence of 2 drops of DMF for 2.5 hours. The excess thionyl chloride and the solvent were removed by distillation in vacuo. The residue was dissolved in 25 ml of methylene chloride. To this solution of the acid chloride were added dropwise 0.7 g of N-methylaniline (0.1 mol) and 13.8 ml (0.1 mol) of triethylamine in 100 ml of methylene chloride within 3 0 minutes. The reaction mixture is left to stand overnight and then 100 ml of water are added. The phases are separated, and the organic phase is washed successively with 50 ml each of 1N HCl, saturated $NaHCO_3$ solution and water. After drying with anhydrous magnesium sulfate, the solvent is evaporated in vacuo, and the residue is triturated with diisopropyl ether and is filtered off with suction. 30.1 g of crystals of melting point 84°–86° C. are obtained. H NMR ($CDCl_3$): $\delta$=6.4–7.5 (m,9H), 6.23 (s,1H), 3.27 (s,3H), 3.2 (s,3H), 2.08 (s,3H).

(b) N-Methyl-N-phenyl-2-methoxymandelamide 19.5 g of the 0-acetyl compound obtained above are stirred in 100 ml of methanolic ammonia at room temperature for 12 hours. After removal of the solvent by evaporation, an oil is obtained and crystallizes on standing. Yield 14.9 g. The product after recrystallization from isopropanol melts at 93°–94°.

Calculated ($C_{16}H_{17}NO_3$) C 70.8, H 6.3, N 5.2; Found C 71.0, H 6.2, N 5.1.

(c) 1-Methyl-3-(2-methoxyphenyl)indolin-2-one 32.2 g (0.12 mol) of N-methyl-N-phenyl-2-methoxymandelamide are introduced into 325 g of polyphosphoric acid at 50° C. The mixture is heated at 110°–120° C. for 3 hours, with stirring, and is then poured into 1.5 liters of icewater. The mixture is extracted twice with 500 ml of methylene chloride each time, and the organic phases are washed twice with water, dried, and concentrated in vacuo. The oily residue crystallizes on trituration with cyclohexane. Yield 25.2 g, melting point 100°–102° C.

$^1H$ NMR ($CDCl_3$) $\delta$=7.4–6.6 (m,8H), 4.8 (s,1H), 3.65, (s,3H), 3.23 (s,3H).

(d)
3-Benzyl-1-methyl-3-(2-methoxyhenyl)indolin-2-one 20.24 g (0.08 mol) of 1-methyl-3-(2-methoxyphenyl)indolin-2-one are dissolved in 200 ml of dry THF. Then 9.2 g (0.08 mol) of potassium tertiary-butylate are added, and the mixture is stirred at room temperature for 15 minutes. At 10°, a solution of 12.1 ml of benzyl bromide in 20 ml of dry THF is added dropwise, and the mixture is then stirred at room temperature for 3 hours. It is then concentrated in vacuo, the residue is partitioned between water and ethyl acetate, and the organic phase is washed twice with water, dried and concentrated. 26.1 g of product of melting point 174°–176° C. are obtained.

$^1H$ NMR ($CDCl_3$) $\delta$=6.2–7.4 (m,12H), 7.5–7.8 (m,1H), 3.5 (s,2H), 3.33 (s,3H), 2.75 (s,3H).

(e)
3-Benzyl-3-(2-hydroxyphenyl)-1-methylindolin-2-one 25 g (0.073 mol) of 3-benzyl-1-methyl-3-(2-methoxyphenyl)- indolin-2-one are dissolved in 250 ml of methylene chloride. The solution is cooled to 0°–5° and a solution of 7 ml (0.074 mol) of boron tribromide in 50 ml of methylene chloride is added dropwise over the course of 30 minutes, and the mixture is then stirred at room temperature for 1 hour and poured onto icewater. The organic phase is separated off, washed twice with water, dried over magnesium sulfate and concentrated. 17.8 g of crystalline product of melting point 188°–190° C. are obtained.

$H$ NMR ($CDCl_3$) $\delta$=6.4–7.3 (m,13H), 3.62 (AB,2H), 2.9 (s,3H).

(f)
3-Benzyl-3-[2-(4-bromobutoxy)phenyl]-1-methylindolin-2-one 16.5 g (0.05 mol) of 3-benzyl-3-(2-hydroxyphenyl)-1-methylindolin-2-one in 250 ml of 2-butanone are stirred under reflux with 20.7 g (0.15 mol) of ground anhydrous potassium carbonate and 17.2 ml (0.15 mol) of 1,4-dibromobutane for 5 hours. The hot mixture is filtered with suction, and the filtrate is concentrated in vacuo. The crystalline residue is triturated with petroleum ether, and the product is isolated after removal of the solvent with suction. 19.3 g of product of melting point 174°–5° C. are obtained.

$^1H$ NMR ($CDCl_3$) $\delta$=6.2–7.3 (m,12H), 7.5–7.8 (m,1H), 2.7 (s,3H), 1.2–4.6 (m,4H).

(g)
3-Benzyl-3-[2-(4-(N-(2-(3,4-dimethoxyphenyl)ethyl)-N-methylamino)butoxy)phenyl]-1-methylindolin-2-one hydrochloride 5.56 g (0.012 mol) of the bromobutyl compound in 30 ml of DMF are heated at 80°–90° C. with 1.66 g (0.012 mol) of ground potassium carbonate and 3.51 g (0.018 mol) of N-methylhomoveratrylamine for 6 hours. The mixture is poured onto 250 ml of water, and the precipitate is filtered off with suction. The crude product is purified by chromatography on 250 g of silica gel using methylene chloride/methanol 9:1 as the mobile phase. The purified product is converted into the hydrochloride using ethereal HCl. Melting point 135°–137° C.

Calculated ($C_{37}H_{43}ClN_2O_4$) C 72.2, H 7.0, N 4.6, Cl 5.8; Found C 71.9, H 7.1, N 4.2, Cl 5.6.

$^1$H NMR (Base in CDCl$_3$) δ=6.2–7.4 (m,15H), 7.5–7.8 (m,1H), 3.0–4.0 (m,4H), 3.83 (s,6H), 2.73 (s,3H), 2.40 (s,3H), 1.0–1.5 (m,4H)

IC$_{50}$ value in the nitrendipine displacement test: $8\times 10^{-6}$M

EXAMPLE 2

3-Benzyl-1-methyl-3-[2-(4-(4.(2-(3,4,5-trimethoxyphenyl)ethyl)piperazinyl)butoxy)phenyl]indolin-2-one dihydrochloride Preparation in analogy to Example 1(g) from 3-benzyl-3-[2-(4-bromobutoxy)phenyl]-1-methylindolin-2-one and 1-[2-(3,4,5-trimethoxyphenyl)ethyl]piperazine.

The dihydrochloride melts at 165°–167° C.

Calculated (C$_{41}$H$_{51}$C$_{12}$N$_3$O$_5$) N 5.7, Cl 9.6; Found N 5.4, Cl 9.6.

$^1$H NMR (Base in CDCl$_3$): δ=6.2–7.5 (m,12H), 7.5–7.85 (m,1H), 3.1–4.0 (m,13H), 2.0–3.0 (m,11H), 2.72 (s,3H), 1.0–1.5 (m,4H).

IC$_{50}$ value: $1\times 10^{-6}$M

EXAMPLE 3

3-[2-(4-(N-(2-(3,4-dimethoxyphenyl)ethyl)-N-methylamino)butoxy)-phenyl]-3-isopropyl-1-methylindolin-2-one hydrochloride (a)

3-(Isopropyl-3-(2-methoxyphenyl)-1-methylindolin-2-one 35.4 g (0.14 mol) of 3-(2-methoxyphenyl)-1-methylindolin--2-one in 350 ml of dry THF are stirred with 16.1 g (0.14 mol) of potassium tertiary-butylate at room temperature for 15 minutes. Then at 10° C., a solution of 14.3 ml of 2-iodopropane in 70 ml of dry THF are added dropwise, and the mixture is then stirred at room temperature for 4 hours. The reaction mixture is left to stand overnight and then partitioned between water and ethyl acetate. After the organic phase has been evaporated, 4.8 g of product of melting point 113°–115° C. are obtained.

$^1$H NMR (CDCl$_3$): δ=7.3–7.5 (m,1H), 6.5–7.3 (m,7H), 3.42 3.2 (s,3H), 2.9 (m,1H), 0.92 (dd,6H).

(b)

3-(2-Hydroxyphenyl)-3-isopropyl-1-methylindolin-2-one

A solution of 1.92 ml (0.02 mol) of boron tribromide in 20 ml of methylene chloride is added dropwise over the course of 1 hour to 5.9 g (0.02 mol) of 3-isopropyl-3-(2-methoxyphenyl)-1-methylindolin-2-one in 75 ml of methylene chloride at 0° C. After 30 minutes, the mixture is poured onto ice-water, and the organic phase is washed with water, dried and evaporated. The residue is triturated with cold toluene and is filtered off with suction. 4.8 g, melting point 172°–174° C.

$^1$H NMR (CDCl$_3$): δ=10.7 (s,1H), 6.4–7.6 (m,8H), 3.45 (m,1H), 3.2 (s,3H), 0.7 (dd,6H).

(c)

3-[2-(4-bromobutoxy)phenyl]-3-isopropyl-1-methylindolin-2-one 19.7 g (0.07 mol) of the hydroxyphenyl compound in 250 ml of 2-butanone are heated to boiling, while stirring, with 29 g (0.21 mol) of ground potassium carbonate and 24.8 ml (0.21 mol) of dibromobutane for 4 hours. The resulting precipitate is filtered off with suction, and the filtrate is evaporated in vacuo, finally under high vacuum. The residue crystallizes on standing. It is stirred with petroleum ether and filtered off with suction. 23.8 g, melting point 98°–100° C.

$^1$H NMR (CDCl$_3$): δ=6.5–7.6 (m,8H), 3.25 (s,3H), 2.5–4.0 (m,5H), 1.3–1.7 (m,4H), 0.95 (dd, 6H).

(d)

3-[2-(4-(N-(2-(3,4-dimethoxyphenyl)-ethyl)-N-methylamino)butoxy)phenyl]-3-isopropyl-1-methylindolin-2-one hydrochloride 5.0 g (0.012 mol) of the bromobutoxy derivative in 30 ml of DMF are heated at 80°–90° C. with 1.66 g (0.012 mol) of potassium carbonate and 3.51 g (0.018 mol) of N-methylhomoveratrylamine for 5 hours. The mixture is poured onto ice-water and extracted three times with ethyl acetate. The combined organic phases are washed twice with water, dried and concentrated. The crude product is purified by chromatography on 250 g of silica gel using methylene chloride/methanol 9:1 as the eluent. After conversion into the hydrochloride, the compound melts at 120° C. Calculated (C$_{33}$H$_{43}$ClN$_2$O$_4$): C 69.9, H 7.6, N 4.9, Cl 6.3; Found: C 69.5, H 8.0, N 4.8, Cl 6.5.

$^1$H NMR (Base in CDCl$_3$): δ=7.4–7.7 (m,1H), 6.5–7.4 (m, 10H), 3.85 (s,6H), 2.3 (s,3H), 0.9 (dd,6H).

IC$_{50}$ value: $2.2\times 10^{-8}$M.

EXAMPLE 4

3-Isopropyl-1-methyl-3-[2-(4-(4-(2-(3,4,5-trimethoxy phenyl)ethyl)piperazinyl)butoxy)phenyl]indolin-2-one dihydrochloride Preparation in analogy to Example 3d) from 3-[2-(4-bromobutoxy)phenyl]-3-isopropyl-1-methylindolin-2-one and 1[2-(3,4,5-trimethoxyphenyl)ethyl]piperazine Melting point 223°–225° C.

Calculated (C$_{37}$H$_{51}$C$_{12}$N$_3$O$_5$) N 6.1, Cl 10.3; Found N 5.9, Cl 10.2.

$^1$H NMR (Base in CDCl$_3$): δ=7.4–7.65 (m,1H), 6.2–7.4 (m,9H), 3.80 and 3.83 (2s,9H), 3.23 (s,3H), 1.16–1.6 (m,4H), 0.9 (dd,6H).

IC$_{50}$ value: $5\times 10^{-9}$M.

EXAMPLE 5

3-[2-(4-(4-(4-bis(4-fluorophenyl)butyl)-1-piperazinyl)-butoxy)phenyl]-3-isopropyl-1-methylindolin-2-one dihydrochloride Preparation in analogy to Example 3d) from 3-[2-(4-bromobutoxy)phenyl]-3-isopropyl-1-methylindolin-2-one and 1[4-bis(4-fluorophenyl)butyl]piperazine Melting point 180°–1° C.

Calculated (C$_{42}$H$_{51}$F$_2$C$_{12}$N$_3$O$_2$): C 68.3, H 7.0, N 5.7; Found: C 67.9, H 7.0, N 5.4.

IC$_{50}$ value: $1.3\times 10^{-8}$M.

EXAMPLE 6

3-Isopropyl-1-methyl-3-[2-(4-(4-(3,4,5-trimethoxybenzyl)- 1-piperazinyl)butoxy)phenyl]indolin-2-one dichydrochloride Preparation in analogy to Example 3(d) from 3-[2-(4-bromo butoxy)phenyl]-3-isopropyl-1-methylindolin-2-one and 3,4,5-trimethoxybenzylpiperazine Melting point 235°–7° C.

Calculated (C$_{37}$H$_{49}$C$_{12}$N$_3$O$_5$): C 64.7, H 7.2, N 6.1, Cl 10.3; Found: C 64.5, H 7.2, N 6.2, Cl 10.5.

IC$_{50}$ value: $4.4\times 10^{-8}$M.

EXAMPLE 7

3-Isopropyl-1-methyl-3-[4-(4-(3,4,5-trimethoxy-phenylacetyl)-1-piperazinyl)butoxyphenyl)indolin-2-one hydrochloride Preparation in analogy to Example 3(d) from 3-12-(4-bromobutoxy)-phenyl]-3-isopropyl-1-methylindolin-2-one and 3,4,5-trimethoxyphenylacetylpiperazine Melting point 140° C. (decomposition)

Calculated ($C_{37}H_{48}ClN_3O_6$): C 66.7, H 7.3, N 6.3, Cl 5.3; Found: C 66.9, H 7.3, N 6.0, Cl 5.4.

IC$_{50}$ value: $4.2 \times 10^{-8}$M.

EXAMPLE 8

1,5-Dimethyl-3-isopropyl-3-[4-(4-(2-(3,4,5-trimethoxy-phenyl)ethyl)piperazinyl)butoxy)phenyl]indolin-2-one dihydrochloride Preparation in analogy to Example 3d) from 3-[2-(4-bromobutoxy)phenyl]-1,5-dimethyl-3-isopropylindolin-2-one and 1-[2-(3,4,5-trimethoxyphenyl)ethyl]piperazine, melting point 242° C.

Calculated ($C_{38}H_{53}Cl_2N_3O_5$) C 64.9, H 7.6, N 6.0, Cl 10.1; Found: C 64.6, H 7.4, N 6.1, Cl 9.9.

$^3$H-Nitrendipine binding test

The test of the activity of substances in the $^3$H-nitrendipine binding test was carried out in a membrane preparation obtained from the cortex of the rat brain and washed several times, the method used essentially being that described by R. J. Gould et al. (Proc. Natl. Acad Sci. U.S.A. 79, 3656 [1982]). The membrane suspension was diluted 1:1500 with TRIS buffer pH 7.4 (50 mM TRIS.HCl, 150 mM NaCl, 1.0 mM CaCl$_2$ and 0.001% by weight, based on TRIS.HCl, NaCl and CaCl$_2$ in solution, of a neutral surface-active substance such as, for example, Genapol ™ ) was incubated in 5 ml portions with $^3$H-nitrendipine (0.1 nM in the test, specific activity 81.3 Ci/mmol) in a shaking water bath at 25° C. for 60 min. The membrane fractions were removed by vacuum filtration through Whatman GF/F glass fiber filters, and the radioactivity was measured in a liquid scintillation counter. The unspecific $^3$H-nitrendipine binding was determined in the presence of 1 μM nifedipine.

The following substances were prepared in analogy to the compounds mentioned in the examples listed:

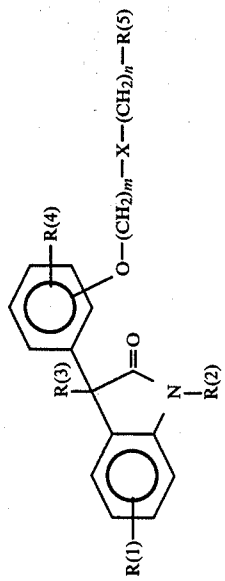
| Example No. | R¹ | R² | R³ | R⁴ | Ether side-ch. in pos. | m | X | n | R⁵ | NMR |
|---|---|---|---|---|---|---|---|---|---|---|
| 9 | H | CH₃ | i-C₃H₇ | H | 2' | 3 | CH₂ | 0 | N-piperidinyl-CH₂-(3,4,5-triOCH₃-phenyl) | 7.4–7.6(m,1H), 6.5–7.4(m,7H), 6.5(s,2H), 3.2(s,3H), 1.3–1.7(m,4H), 0.9(dd,6H) |
| 10 | H | CH₃ | n-C₆H₁₃ | H | 2' | 3 | " | " | N-piperidinyl-CH₂-CH₂-(3-OCH₃-phenyl) | 7.4–7.65(m,1H), 6.4–7.4(m,11H), 3.8(s,3H), 3.3(s,3H), 1.0–1.7(m,12H), 0.85(m,3H) |
| 11 | H | CH₃ | n-C₁₂H₂₅ | H | 2' | 3 | " | " | N-piperidinyl-CH₂-CH₂-(3,5-diOCH₃-phenyl) | 6.3–7.7(m,11H), 3.5–3.9(s,6H=m,2H), 1.0–1.8(m,24H),0.87(m,3H) |
| 12 | H | CH₃ | CH₂–CH=CH₂ | H | 2' | 3 | " | " | N-piperidinyl-CH₂-(3,4,5-triOCH₃-phenyl) | 6.5–7.7(m,8H), 6.45(s,2H), 3.8 + 3.85(2s,9), 5.0–5.9(m,3H),3.2–3.7(m+s,7H), 2.0–3.1 (m,14H), 1.3–1.7(m,4H) |

-continued
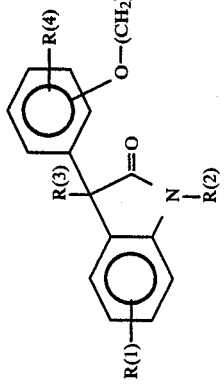
| Example No. | R¹ | R² | R³ | R⁴ | Ether side-ch. in pos. | m | X | n | R⁵ | NMR |
|---|---|---|---|---|---|---|---|---|---|---|
| 13 | H | CH₃ | i-C₃H₇ | H | 2' | 3 | " | " | 3,5-dimethoxyphenyl-4-hydroxypiperidine | 7.4–7.65(m,1H), 6.4–7.4(m,10H),3.84(s,6H), 3.3(s,3H),0.9(dd,6H) |
| 14 | H | CH₃ | cyclohexyl-CH₂ | H | 2' | 3 | " | " | N-piperidinyl-(CH₂)₃-CH(4-F-phenyl)₂ | 7.4–7.7(m,1H),6.5–7.4(m,15H),3.7(t,3H), 2.3–3.0(m,13H), 1.1–1.7(m,18H) |
| 15 | H | C₂H₅ | cyclohexyl-CH₂ | H | 2' | 3 | CH₂ | O | 3,4-dimethoxyphenyl-CH(CH₃)-N(CH₃)-CH₂ | 6.5–7.65(m,11H), 3.84(s,6H), 2.35(s,3H), 0.85–1.8(m,21H) |
| 16 | H | C₃H₇ | 4-F-phenyl-CH₂ | H | 2' | 3 | " | " | 3-methoxyphenyl-N(CH₃)-(CH₂)₂ | 6.5–7.7(m,16H), 3.8(s,3H), 3.3–3.9(m,6H) 2.35(s,3H), 0.95(t,3H) |

-continued

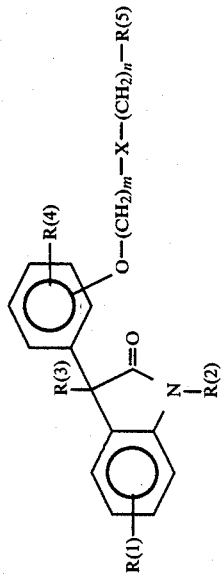

| Example No. | R¹ | R² | R³ | R⁴ | Ether side-ch. in pos. | m | X | n | R⁵ | NMR |
|---|---|---|---|---|---|---|---|---|---|---|
| 17 | H | CH₃ | i-C₃H₇ | H | 2' | 3 | " | " | piperidine-N-(CH₂)₃- attached to 3,4,5-trimethoxyphenyl | 7.4–7.65(m,1H),6.5–7.4(m,7H), 6.4(s,2H) 3.8–3.9(2s,9H), 1.2–1.7(m,6H),0.9(dd, 6H) |
| 18 | H | CH₂–C₆H₅ | C₂H₅ | H | 2' | 3 | " | " | piperidine-N- attached to 2-ethoxyphenyl | 6.5–7.7(m,17H), 4.0(q,2H), 3.65(t,2H), 2.3–3.5(m,12H), 1.42(t,3H), 0.9(t,3H) |
| 19 | H | CH₃ | i-C₃H₇ | H | 2' | 4 | " | " | piperidine-N-CH₃ with 3,4,5-trimethoxyphenyl | 7.4–7.65(m,1H),6.5–7.4(m,7H),6.4(s, 2H), 3.8+3.85(2s,9H),3.3(s,3H), 1.1–1.6 (m,6H), 0.9(dd,6H) |
| 20 | H | CH₃ | i-C₃H₇ | H | 2' | 3 | " | " | N(CH₃)–CH₂–piperidinyl–4, attached via CH₂ to 3,4,5-trimethoxyphenyl | 6.5–7.65(m,8H), 6.4(s,2H), 3.8+3.85(2s, 9H), 3.3(s,3H), 2.3(s,3H), 0.95(dd,6H) |

-continued

| Example No. | R¹ | R² | R³ | R⁴ | Ether side-ch. in pos. | m | X | n | R⁵ | NMR |
|---|---|---|---|---|---|---|---|---|---|---|
| 21 | H | CH₃ | n-C₃H₇ | H | 2' | 3 | CH₂ | 0 | piperazine-N-CH₂-CH₂-N with 3,4,5-tri-OCH₃ phenyl, N-CH₃ | 6.5–7.7(m,8H), 6.4(s,2H), 3.8+3.83(2s, 3H), 0.9(t,3H) |
| 22 | H | CH₃ | i-C₃H₇ | H | 3' | 2 | " | " | piperazine-N-CH₂-CH=CH-phenyl | 7.4–7.6(m,1H), 6.0–7.4(m,14H), 3.7(m,2H), 3.2(s,3H), 3.1–3.4(m,2H), 0.95(dd,6H) |
| 23 | H | CH₃ | i-C₃H₇ | H | 3' | 2 | " | " | piperazine-N-(3-OCH₃-phenyl) | 6.4–7.6(m,12H), 3.7(s,3H), 2.3–3.8(m,13H), 3.3(s,3H), 0.9(dd,6H) |
| 24 | 7-CH₃ | CH₃ | CH₂—CH₂—phenyl | H | 2' | 3 | " | " | piperazine-N-CH₂-(3-CF₃-phenyl) | 6.5–7.4(m,16H), 2.2–3.8(m,24H), 1.3–1.7(m,4H) |

-continued
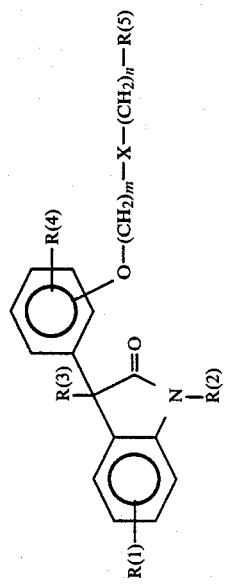
| Example No. | R¹ | R² | R³ | R⁴ | Ether side-ch. in pos. | m | X | n | R⁵ | NMR |
|---|---|---|---|---|---|---|---|---|---|---|
| 25 | H | $CH_3$ | $n-C_3H_7$ | H | 2' | 3 | " | " | piperidine-N-CH with two 4-OCH₃ phenyl groups | 6.4–7.6(m,16H), 3.8(s,6H), 3.2(s,3H), 2.2–3.8(m,14H), 1.3–1.7(m,6H), 0.9(t,3H) |
| 26 | H | $CH_3$ | $i-C_3H_7$ | 3'-$OCH_3$ | 2' | 3 | " | " | piperidine-N-(CH₂)₂ with 3-OCH₃ phenyl | 7.4–7.7(m,1H), 6.4–7.4(m,10H), 3.8+3.85 (2s,6H), 2.2–3.2(m,15H), 0.9(dd,6H) |
| 27 | H | $CH_3$ | $i-C_3H_7$ | 3'-$OCH_3$ | 2' | 3 | " | " | piperidine-N-(CH₂)₂ with 2,4-di-OCH₃ phenyl | 6.4–7.7(m,10H), 3.80–3.85(3s,9H), 3.3 (s,3H), 2.3(s,3H), 0.9(dd,6H) |
| 28 | H | $CH_3$ | $C_2H_5$ | H | 4' | 1 | $CH_2$ | 0 | piperidine-N-(CH₂)₃-CH with two 4-F phenyl groups | 7.4–7.65(m,1H), 6.4–7.4(m,15H), 3.4–4.1 (m,3H), 3.4(s,3H), 1.8–3.0(m,16H), 1.1 (t,3H) |

-continued

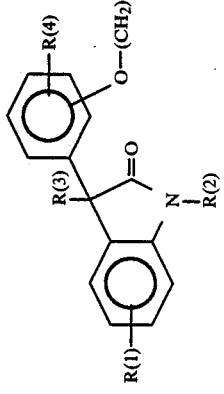

| Example No. | R¹ | R² | R³ | R⁴ | Ether side-ch. in pos. | m | X | n | R⁵ | NMR |
|---|---|---|---|---|---|---|---|---|---|---|
| 29 | H | CH₃ | 3-methoxybenzyl (Ph-CH₂ with OCH₃) | CH₃ | 4' | 2 | " | " | 3-methoxyphenyl-CH₂-NH-(4-piperidinyl) | 6.4–7.7(m,16H), 3.8+3.85(2s,6H), 3.(s,3H), 2.25(s,3H) |
| 30 | H | CH₃ | 4-fluorobenzyl (Ph-CH₂ with F) | H | 2' | 3 | " | " | 4-(3,4,5-trimethoxybenzoyl)piperidine | 7.4–7.6(m,1H), 6.5–7.4(m,11H), 6.4(s, 2H), 3.8 und 3.85(2s,9H), 3.2(s,2H), 2.6–3.8(m,13H) |
| 31 | H | CH₃ | i-C₃H₇ | H | 2' | 3 | " | " | 4-(3,4,5-trimethoxybenzoyl)-N-methylpiperazine | 7.4–7.7(m,1H), 6.5–7.4(m,7H), 6.4(s, 2H), 3.8(s,9H), 3.7(m,2H), 3.2(s,3H), 2.3(s,3H), 0.9(dd,6H) |
| 32 | H | CH₃ | i-C₃H₇ | H | 2' | 3 | " | " | 4-(hexanoyl)piperazine (N-CO-C₅H₁₁) | 7.4–7.6(m,1H), 6.5–7.4(m,7H), 3.2(s, 3H), 0.9(dd,6H), 0.85(t,3H) |

-continued

![Structure: R(1)-phenyl-C(R(3))(phenyl-R(4)-O-(CH2)m-X-(CH2)n-R(5))-C(=O)-N(R(2))]

| Example No. | R¹ | R² | R³ | R⁴ | Ether side-ch. in pos. | m | X | n | R⁵ | NMR |
|---|---|---|---|---|---|---|---|---|---|---|
| 33 | H | CH₃ | i-C₃H₇ | H | 2' | 3 | " | " | [N-piperidinyl-N(CH₃)-CO-CH₂-(3,4-di-OCH₃-phenyl)] | 7.4-7.6(m,1H), 6.5-7.4(m,10H), 3.8(s,6H), 3.2(s,3H), 2.8(s,3H), 0.9(dd,6H) |
| 34 | H | CH₃ | C₂H₅ | H | 2' | 3 | C=O | 0 | [N-piperidinyl-CH₂-(3,4,5-tri-OCH₃-phenyl)] | 6.5-7.7(m,8H), 6.4(s,2H), 3.80, 3.83 (2s,9H), 3.2(s,3H), 1.1(t,3H) |
| 35 | H | CH₃ | i-C₃H₇ | H | 2' | 2 | O | 2 | [N-methylpiperazinyl] | 7.4-7.6(m,1H), 6.5-7.4(m,7H), 3.5-4.1(m,6H), 3.2(s,3H), 2.4(s,3H), 1.0(dd,6H) |
| 36 | H | CH₃ | n-C₆H₁₃ | H | 2' | 1 | CH(OH) | 1 | [N-piperidinyl-CH₂-(3,4,5-tri-OCH₃-phenyl)] | 7.4-7.7(m,1H), 6.5-7.4(m,7H), 6.4(s,2H), 3.8 and 3.85(2s,9H), 3.2(s,3H), 0.85(t,3H) |
| 37 | H | CH₃ | i-C₃H₇ | H | 2' | 2 | S | 2 | [N-piperidinyl-CH₂-(3-OCH₃-phenyl)] | 6.4-7.7(m,12H), 3.8(s,3H), 3.2(s,3H), 2.3-4.0(m,21H), 0.95(dd,6H) |

We claim:
1. A compound of the formula I

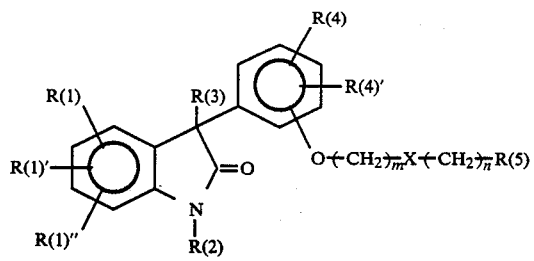

in which
R(1), R(1)', and R(1)" are identical or different and are independent of one another and are hydrogen, $(C_1-C_4)$-alkyl, $(C_1-C_3)$-alkoxy, F, Cl, Br, $CF_3$, nitro, hydroxyl, acetamido or amino,
R(2) is hydrogen, $(C_1-C_{10})$-alkyl, $(C_3-C_{10})$-alkenyl, phenyl-$(C_1-C_4)$-alkyl, the phenyl ring being unsubstituted or substituted by one, two or three substituents from the group consisting of $(C_1-C_4)$-alkyl, $(C_1-C_3)$-alkoxy, F, Cl, $CF_3$, $(C_1-C_2)$-alkylenedioxy and nitro,
R(3) is hydrogen, $(C_1-C_{15})$-alkyl, $(C_3-C_{15})$-alkenyl, $(C_4-C_8)$-cycloalkyl, $(C_4-C_8)$-cycloalkyl-$(C_1-C_4)$-alkyl, phenyl or phenyl-$(C_1-C_4)$-alkyl, the phenyl radical being unsubstituted or substituted by one, two or three substituents from the group consisting of $(C_1-C_4)$-alkyl, $(C_1-C_3)$-alkoxy, F, Cl, $CF_3$, $(C_1-C_2)$-alkylenedioxy and nitro,
R(4) and R(4)' are, independently of, one another, identical or different hydrogen, $(C_1-C_4)$-alkyl, $(C_1-C_3)$-alkoxy, F, Cl, $CF_3$, nitro, hydroxyl, acetamido or amino,
m is 1, 2, 3, or 4,
n is 0, 1, 2 or 3, but where X is a heteroatom n is only 2 or 3
X is a $CH_2$ group, oxygen, sulfur, a carbonyl group, a CH(OH) group or a group

in which
R(15) and R(15)' are identical or different and are hydrogen or $(C_1-C_4)$-alkyl,
R(5) is

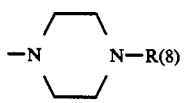

in which
R(8) is hydrogen, $(C_1-C_{10})$-alkyl, $(C_1-C_8)$-alkanoyl, pyridyl, phenyl, phenyl-$(C_1-C_4)$-alkyl, phenyl-$(C_3-C_5)$-alkenyl, benzhydryl or benzhydryl-$(C_1-C_4)$-alkyl, phenyl-$(C_1-C_4)$-alkanoyl or benzoyl, the phenyl radicals each being unsubstituted or substituted by one, two or three radicals from the group consisting of $(C_1-C_4)$-alkyl, $(C_1-C_4)$-alkoxy, $(C_1-C_2)$-alkylenedioxy, F, Cl, Br, $CF_3$ and hydroxyl, or a salt of the compound of the formula I with a pharmaceutically acceptable acid.

2. A compound as claimed in claim 1 wherein
R(1) and R(1)' are identical or different and, independently of one another, are hydrogen, methyl, ethyl, methoxy, ethoxy, fluorine, chlorine, $CF_3$, nitro or acetamido,
R(1)" is hydrogen,
R(2) is hydrogen, $(C_1-C_6)$-alkyl, allyl, methallyl, benzyl, phenethyl, 4-methoxybenzyl, 3,4-dimethoxybenzyl, 3,4,5-trimethoxybenzyl or 3,4-methylenedioxybenzyl,
R(3) is hydrogen, $(C_1-C_{12})$-alkyl, allyl, methallyl, $(C_5-C_7)$-cycloalkyl, $(C_5-C_7)$-cycloalkyl-$(C_1-C_4)$-alkyl, benzyl, methylbenzyl, fluorobenzyl, methoxybenzyl, dimethoxybenzyl or phenylethyl,
R(4) is hydrogen, methyl, methoxy, ethoxy, chlorine, nitro, hydroxyl, acetamido or amino,
R(4)' is hydrogen,
m is 1, 2, 3 or 4,
n is 0, 1, 2 or 3, but where X is a heteroatom n is only 2 or 3
X is a $CH_2$ group, oxygen, sulfur, a carbonyl group, a CH(OH) group or a group

in which
R(15) and R(15)' are identical or different and are hydrogen, methyl or ethyl,
R(5) is

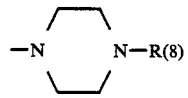

in which
R(8) is hydrogen, $(C_1-C_6)$-alkyl, $(C_1-C_6)$-alkanoyl, phenyl, the phenyl radical being unsubstituted or substituted by one or two radicals from the group consisting of $(C_1-C_4)$-alkyl, $(C_1-C_4)$-alkoxy, $(C_1-C_2)$-alkylenedioxy, F, Cl, $CF_3$ and hydroxyl, or is phenyl-$(C_1-C_4)$-alkyl, phenyl-$(C_3-C_5)$-alkenyl, benzhydryl or benzhydryl-$(C_1-C_4)$-alkyl, phenyl-$(C_1-C_4)$-alkanoyl or benzoyl, the phenyl radicals each being unsubstituted or substituted by one, two or three radicals from the group consisting of methyl, ethyl, methoxy, ethoxy, $(C_1-C_2)$-alkylenedioxy, F, Cl, $CF_3$ and hydroxyl,
or a salt of the compound of the formula I with a pharmaceutically acceptable acid.

3. A compound as claimed in claim 1, wherein
R(1) is hydrogen, methyl, methoxy, fluorine or chlorine,
R(1)' is hydrogen or methoxy,
R(1)" is hydrogen,
R(2) is hydrogen, methyl, ethyl, propyl, isopropyl, butyl, sec. butyl, isobutyl, benzyl or phenethyl,
R(3) is hydrogen, $(C_1-C_{12})$-alkyl, cyclopentyl, cyclohexyl, cyclopentylmethyl, cyclohexylmethyl, allyl, methallyl, benzyl, methylbenzyl, fluorobenzyl, methoxybenzyl, dimethoxybenzyl or phenylethyl, R(4) is hydrogen, methoxy, methyl, chlorine, nitro or hydroxyl, R(4)' is hydrogen, m is 1,2 or 3, n is 0, 1 or 2 but where X is a heteroatom n is only 2

X is a $CH_2$ group, oxygen, a carbonyl group, a CH(OH) group or a group

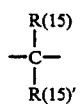

in which

R(15) and R(15), are identical or different and are hydrogen or methyl,

R(5) is

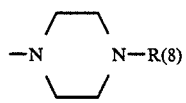

in which

R(8) is $(C_1-C_6)$-alkyl, $(C_1-C_6)$-alkanoyl, phenyl, phenyl-$(C_1-C_4)$-alkyl, benzhydryl or benzhydryl-$(C_1-C_4)$-alkyl, phenyl-$(C_1-C_4)$ alkanoyl or benzoyl, the phenyl radicals each being unsubstituted or substituted by one, two or three radicals from the group consisting of methyl, methoxy, ethoxy, methylenedioxy, fluorine, chlorine and hydroxyl, or a salt of the compound of the formula I with a pharmaceutically acceptable acid.

4. A pharmaceutical composition for the treatment of a calcium balance disturbance in a warm-blooded animal comprising an effective amount for said treatment of a compound I as claimed in claim 1 or a pharmaceutically acceptable salt thereof together with a pharmaceutically acceptable carrier.

5. A process for the treatment of a calcium balance disturbance in a warm-blooded animal which comprises administering to the warm-blooded animal an effective amount for said treatment of a compound I as claimed in claim 1 or a pharmaceutically acceptable salt thereof with or without a pharmaceutically acceptable carrier.

* * * * *